(12) United States Patent
Navia et al.

(10) Patent No.: US 7,087,079 B2
(45) Date of Patent: Aug. 8, 2006

(54) METHOD AND APPARATUS FOR REPLACING A MITRAL VALVE WITH A STENTLESS BIOPROSTHETIC VALVE

(75) Inventors: Jose' Luis Navia, Shaker Hts., OH (US); Jose' A. Navia, Buenos Aires (AR); Jorge L. Jordana, Buenos Aires (AR)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/683,105

(22) Filed: Oct. 10, 2003

(65) Prior Publication Data

US 2004/0122512 A1    Jun. 24, 2004

Related U.S. Application Data

(60) Provisional application No. 60/417,912, filed on Oct. 10, 2002.

(51) Int. Cl.
  *A61F 2/24*    (2006.01)
(52) U.S. Cl. .................. 623/2.16; 623/1.26; 623/904
(58) Field of Classification Search ............... 606/159, 606/167; 623/2.1, 2.12, 2.13, 904, 2.16, 623/1.24, 1.26, 1.3, 1.31; 128/898
  See application file for complete search history.

(56) References Cited

U.S. PATENT DOCUMENTS

| | | | |
|---|---|---|---|
| 4,790,844 A | 12/1988 | Ovil | 623/2.13 |
| 4,960,424 A | 10/1990 | Grooters | 128/898 |
| 5,156,621 A | 10/1992 | Navia et al. | 623/2.12 |
| 5,163,954 A | 11/1992 | Curcio et al. | 623/2.41 |
| 5,344,442 A * | 9/1994 | Deac | 623/2.12 |
| 5,415,667 A * | 5/1995 | Frater | 623/2.11 |
| 5,500,015 A | 3/1996 | Deac | |
| 5,554,184 A | 9/1996 | Machiraju | |
| 5,733,331 A | 3/1998 | Peredo | |
| 5,824,067 A * | 10/1998 | Gross | 128/898 |
| 5,928,281 A * | 7/1999 | Huynh et al. | 623/2.14 |
| 6,074,417 A | 6/2000 | Peredo | 623/2.1 |
| 6,312,464 B1 | 11/2001 | Navia | |

(Continued)

OTHER PUBLICATIONS

"Functional Evaluation of the Medtronic Stentless Porcine Xenograft Mitral Valve in Sheep", Paul Dagum, MD, PhD, et al.; Circulation. 1999; 100[suppl II]:II-70-II-77.

(Continued)

*Primary Examiner*—Brian E. Pellegrino
(74) *Attorney, Agent, or Firm*—Tarolli, Sundheim, Covell & Tummino LLP (57) ABSTRACT

A stentless bioprosthetic valve includes at least one piece of biocompatible material comprising a bi-leaflet conduit. The conduit has a distal end and a proximal end that defines a first annulus for suturing to the valve annulus of a heart. The conduit further includes first and second leaflets that mimic the anterior and posterior leaflets of the native mitral valve. The first and second leaflets extend between the proximal and distal ends. The distal end defines a second annulus at which the first and second leaflets terminate. The second annulus is for suturing to free edges of the anterior and posterior leaflets of the native mitral valve that remain intact following resection of the native mitral valve so that the native chordae tendineae continue to provide prolapse prevention and left ventricular muscle support functions in addition to maintaining the continuity between the valve annulus and the papillary muscles. A method for replacing the native mitral valve with a stentless bioprosthetic valve is also provided.

5 Claims, 6 Drawing Sheets

U.S. PATENT DOCUMENTS

| | | | |
|---|---|---|---|
| 6,358,277 B1 | 3/2002 | Duran | |
| 6,409,759 B1 | 6/2002 | Peredo | 623/2.13 |
| 2002/0052651 A1 | 5/2002 | Myers et al. | |
| 2002/0055774 A1* | 5/2002 | Liddicoat | 623/2.38 |
| 2002/0091441 A1 | 7/2002 | Guzik | 623/2.13 |
| 2003/0069635 A1 | 4/2003 | Carledge et al. | |

OTHER PUBLICATIONS

New U.S. Navia et al. patent application for Method and Apparatus for Replacing a Mitral Valve with a Stentless Bioprosthetic Valve Having Chordae, filed Oct. 10, 2003.

* cited by examiner

METHOD AND APPARATUS FOR REPLACING A MITRAL VALVE WITH A STENTLESS BIOPROSTHETIC VALVE

RELATED APPLICATION

This application claims priority from U.S. provisional patent application Ser. No. 60/417,912, filed on Oct. 10, 2002, the subject matter of which is incorporated herein by reference.

TECHNICAL FIELD

The present invention relates to a method and apparatus for replacing a native mitral valve with a stentless bioprosthetic valve.

BACKGROUND OF THE INVENTION

The mitral valve is a functional unit composed of multiple dynamically interrelated units. During cardiac cycle, the fibrous skeleton, the anterior and posterior leaflets, the papillary muscles, the chordae tendineae, and the ventricular and atrial walls all interplay symphonically to render a competent valve. The complex interaction between the mitral valve and the ventricle by the subvalvular apparatus (the papillary muscles and the chordae tendineae is essential in that it maintains the continuity between the atrio-ventricular ring (which is part of the fibrous skeleton of the heart) and the ventricular muscle mass, which is essential for the normal function of the mitral valve.

The chordae tendineae, which connect the valve leaflets to the papillary muscles (PM) act like "tie rods" in an engineering sense. Not only do the chordae tendineae prevent prolapse of the mitral valve leaflets during systole, but they also support the left ventricular muscle mass throughout the cardiac cycle.

To function adequately, the mitral valve needs to open to a large orifice area and, for closure, the mitral leaflets need to have an excess of surface area (i.e. more than needed to effectively close the mitral orifice). On the other hand, systolic contraction of the posterior ventricular wall around the mitral annulus (MA) creates a mobile D-shaped structure with sphincter-like function which reduces its area by approximately 25% during systole, thus exposing less of the mitral leaflets to the stress of the left ventricular pressure and flow.

Although the primary function of the mitral valve is to act as a one-way no return valve, it has been postulated that the structural integrity of the MA-PM continuity is essential for normal left ventricular function.

Since it was first suggested in the mid-1960's that preservation of the subvalvular apparatus during mitral valve replacement might prevent low cardiac output in the early postoperative period, this important observation was largely overlooked by most surgeons for many years.

There is now considerable laboratory and clinical evidence to corroborate this position, as evidence has demonstrated that chordal excision is associated with a change in left ventricular shape from oval to spherical, which can lead to a significant increase in postoperative left ventricular end systolic volume and wall stress, along with a decline in ejection fraction.

The majority of evidence appears to support the concept that preservation of the subvalvular apparatus with the MA-PM continuity in any procedure on the mitral valve is important for the improved long-term quality and quantity of life after mitral valve surgery. Reparative techniques to correct mitral valve disease are often the best surgical approach for dealing with mitral valve abnormalities, however mitral valvuloplasty is not always feasible because of extensive fibrosis, leaflets calcification, or massive chordal rupture. Mitral valve replacement using either a mechanical valve or a bioprosthetic valve thus remains the best surgical solution for severe mitral valve disease.

However, there are many additional problems that face patients after valve replacement with a prosthestic valve. Valve-related problems include limitation of the mitral flow (due to a small effective orifice area) during exercise and high cardiac output imposed by a smaller size artificial valve as compared with the natural valve orifice area.

Further, the rigid structure of an artificial valve prevents the physiologic contraction of the posterior wall of the left ventricle surrounding the MA during systole. Surgical interruption of the MA-PM continuity accounts for changes in geometry mechanics and performance of the left ventricle. Myocardial rupture, a lethal complication of mitral valve replacement, results from excision or stretching of the papillary muscle in a thin and fragile left ventricle. Myocardial rupture can also be caused by a strut of a stented bioprosthetic valve eroding into or protruding through the posterior left ventricle wall. Maintaining the MA-PM continuity appears to provide a substantial degree of protection from this devastating complication. Also, the difficulties in controlling adequate anticoagulation for a mechanical valve bring a high morbidity risk factor of thromboembolic and hemorragic complication and endocarditis.

Stented tissue valves, although less thrombogenic, are not reliably durable and, because of the rigid stent, they are less hemodynamically efficient. Stentless valves are considered to have the potential advantages of superior hemodynamic performance and enhanced durability and have already showed satisfactory mid-term results in the aortic position. From these points of view, it is expected that new stentless valves in the mitral position will be developed. However, stentless mitral valves are not yet commonly available for clinical use because of the anatomical and functional complexity of the mitral valve and the subvalvular apparatus, resulting in the difficulties of the design and implantation procedures of the stentless mitral valves. The present invention provides and apparatus and method for replacing a native mitral valve with a stentless, bioprosthetic valve that maintains the anatomical and functional complexity of the mitral valve and the subvalvular apparatus.

SUMMARY OF THE INVENTION

The present invention is a stentless bioprosthetic valve for replacing a native mitral valve resected from a valve annulus in a heart. The bioprosthetic valve comprises at least one piece of biocompatible material comprising a bi-leaflet conduit having dimensions that correspond to the dimensions of the native mitral valve. The conduit has a proximal end and a distal end. The proximal end defines a first annulus for suturing to the valve annulus of the heart. The conduit further includes first and second leaflets that mimic the three-dimensional anatomical shape of the anterior and posterior leaflets of the native mitral valve. The first and second leaflets extend between the proximal end and the distal end of the conduit. The distal end of the conduit defines a second annulus at which the first and second leaflets terminate. The second annulus is for suturing to free edges of the anterior and posterior leaflets of the native mitral valve that remain intact following resection of the native mitral valve so that the native chordae tendineae, which are attached to the papillary muscles, continue to provide prolapse prevention and left ventricular muscle support functions in addition to maintaining the continuity between the valve annulus and the papillary muscles.

In accordance with one aspect of the invention, the at least one piece of biocompatible material comprises harvested biological tissue.

In accordance with another aspect of the invention, the harvested biological tissue comprises pericardial tissue.

In accordance with yet another aspect of the invention, the harvested biological tissue comprises a porcine mitral valve.

In accordance with still another aspect of the invention, the harvested biological tissue comprises a homograft mitral valve.

In accordance with yet another aspect of the invention, the at least one piece of biocompatible material comprises an artificial tissue.

In accordance with another feature of the invention, the bioprosthetic valve further comprises a biocompatible, unstented ring connected to the first annulus for supporting the first annulus and for suturing to the valve annulus of the heart. The ring, when sutured to the valve annulus, impedes dilatation of the valve annulus and preserves motion of the valve annulus.

The present invention also provides a method for replacing a native mitral valve having anterior and posterior leaflets with a stentless bioprosthetic valve. According to the inventive method, at least one piece of biocompatible material that comprises a bi-leaflet conduit having dimensions that correspond to the dimensions of the native mitral valve being replaced is provided. The conduit has a proximal end and a distal end. The proximal end defines a first annulus and the distal end defines a second annulus. The conduit further includes first and second leaflets that mimic the three-dimensional shape of the anterior and posterior leaflets of the native mitral valve. The first and second leaflets extend from the proximal end and terminate at the distal end of the conduit. The majority of the anterior and posterior leaflets of the native mitral valve are resected from the valve annulus but the free edges of the anterior and posterior leaflets are left intact along with the native chordae, tendineae which are attached to the papillary muscles, so that the native chordae tendineae can provide prolapse prevention and left ventricular muscle support functions for the bioprosthetic valve in addition to maintaining the continuity between the valve annulus and the papillary muscles. The first and second leaflets at the second annulus of the conduit are sutured to the free edges of the anterior and posterior leaflets of the native mitral valve that remain following resection of the native mitral valve. The first annulus of the conduit is then sutured to the valve annulus of the native mitral valve to secure the bioprosthetic valve to the valve annulus.

In accordance with another aspect of the inventive method, a biocompatible, unstented support ring encircles the first annulus. The support ring is sutured to the valve annulus of the heart to secure the bioprosthetic valve to the valve annulus and to impede dilatation of the valve annulus and preserve motion of the valve annulus.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

The present invention relates to a method and apparatus for replacing a native mitral valve with a stentless bioprosthetic valve. As representative of the present invention, FIG. 1 illustrates an apparatus 10 comprising a stentless bioprosthetic valve 12 for replacing a native mitral valve 14 (FIG. 4) in accordance with a first embodiment.

Figure 1:
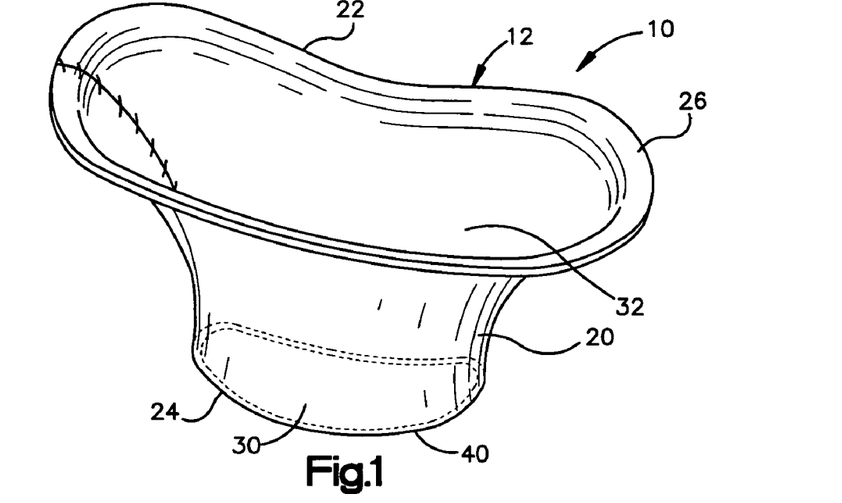
FIG. 1 is a perspective view of a stentless, bioprosthetic valve in accordance with a first embodiment of the present invention.

The bioprosthetic valve 12 shown in FIG. 1 is made from one or more pieces of biocompatible material formed into a bi-leaflet conduit 20 having dimensions that correspond to the dimensions of the native mitral valve 14. The conduit 20 has a proximal end 22 and a distal end 24. The proximal end 22 defines a first annulus 26 for suturing to the valve annulus of the native mitral valve 14, as described further below.

The conduit 20 further includes first and second leaflets 30 and 32 (FIG. 2) that mimic the three-dimensional anatomical shape of the anterior and posterior leaflets 34 and 36 (FIG. 4), respectively, of the native mitral valve 14. The first and second leaflets 30 and 32 extend between the proximal end 22 and the distal end 24 of the conduit 20.

The distal end 24 of the conduit 20 defines a second annulus 40 at which the first and second leaflets 30 and 32 terminate. The second annulus 40 is for suturing to free edges of the anterior and posterior leaflets 34 and 36 of the native mitral valve 14, as described further below.

The biocompatible material of the bioprosthetic valve 12 may be a harvested biological material including, but not limited to, bovine pericardial tissue, horse pericardial tissue, porcine pericardial tissue, a porcine mitral valve, or a homograft (or allograft) mitral valve. The biocompatible material may also be suitable synthetic material including, but not limited to, polyurethane or expanded PTFE.

In the case of, for example, bovine pericardial tissue, the tissue is harvested in slaughterhouses and kept in cold saline solution for transport to minimize the effects of autolysis and bacterial/enzymatic reactions on the tissue. The pericardial tissue is dissected to be clean of all fatty and other biological materials. The pericardial material is then formed into a tri-dimensional shape of what will be the leaflet structure of the bioprosthetic valve 12 by attaching the pericardial tissue to a mold (not shown) having such a shape.

Figure 2:
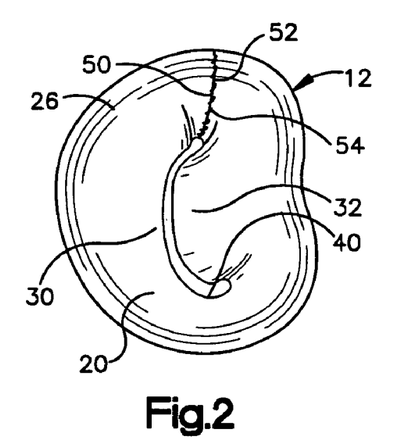
FIG. 2 is a plan view of the valve of FIG. 1 showing the valve in a closed position.
Figure 2A:
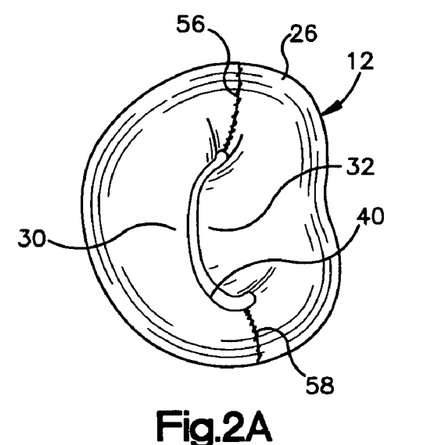
FIG. 2A is view similar to FIG. 2 illustrating an alternate construction for the valve.

The molds are produced in different sizes to render valves of different sizes to match the needs of the different patients (i.e., sizes between 23 and 35 mm in diameter). The molds can have either a male shape of what will be the inflow aspect of the valve 12, or a female aspect of the same. The pericardial tissue is applied to the molds and accommodated to ensure the complete comformability to the mold's shape. The bioprosthetic valve 12 can be made with only one piece of pericardial tissue, as shown in FIGS. 1 and 2. Alternatively, the bioprosthetic valve 12 can be made with two pieces of pericardial tissue, one of which will form the first leaflet 30 and the other forms the second leaflet 32 of the prosthetic valve, as may be seen in FIG. 2A.

Once the pericardial piece(s) is fully conformed on the mold, the biological material is tanned by immersion in an adequate fixation solution (e.g. 0.65% glutaraldehyde solution buffered at pH 7.4). This tanning can be achieved with an ample range of glutaraldehyde concentrations (e.g. between 0.4% and 5%).

Figure 2B:
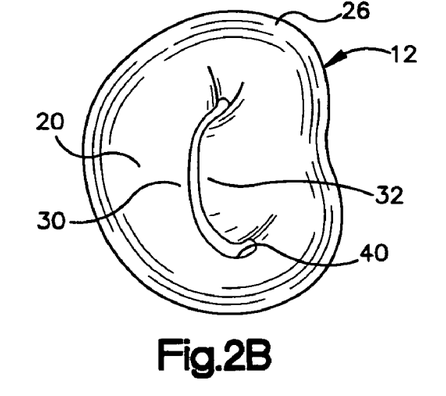
FIG. 2B is view similar to FIG. 2 illustrating another alternate construction for the valve.

When the pericardial tissue is already fixed with the fixation agent, it is then separated from the mold and the lateral edges 50 and 52 (FIG. 2) are sutured together along a seam 54 to form the tubular conduit 20. In the alternate embodiment of FIG. 2A where two pieces of pericardial tissue are used, it is necessary to suture the tissue in two locations, thereby forming two seams 56 and 58. The seams 54, 56, and 58 are always placed at what will be the commissures of the prosthetic valve 12, where the first leaflet 30 meets the second leaflet 32. FIG. 2B illustrates another alternate embodiment for the valve 12 in which there are no seams because the valve is a harvested porcine mitral valve.

Figure 3:
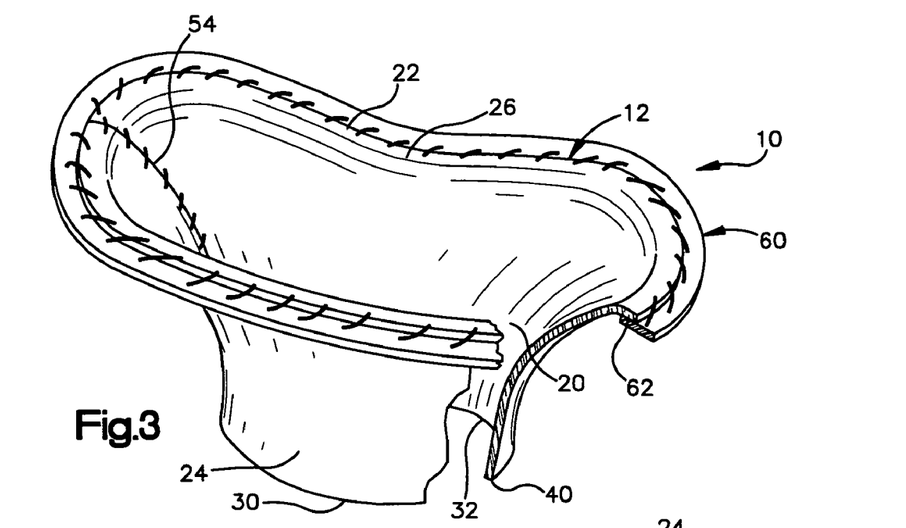
FIG. 3 is a perspective view, partially in section, of the valve of FIG. 1 and illustrating a method for forming a ring at the proximal end of the valve.
Figure 3A:
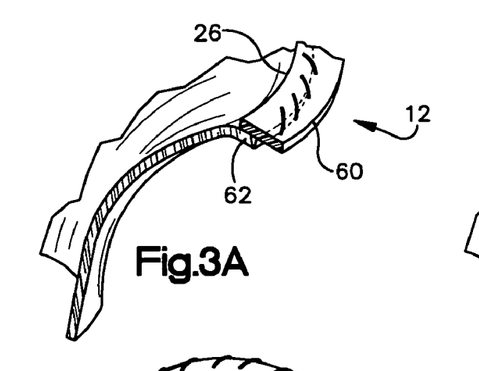
FIG. 3A is a view of a portion of FIG. 3 showing an alternate construction.
Figure 3B:
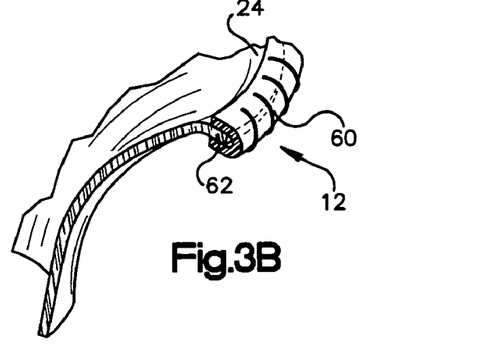
FIG. 3B is a view of a portion of FIG. 3 showing another alternate construction.

In accordance with the first embodiment of the present invention, the valve 12 further includes a flexible, unstented, biocompatible ring 60 (FIG. 3) that is sutured about the first annulus 26 along a proximal edge 62 at the proximal end 22 of the conduit 20. The ring 60 is for supporting the first annulus 26 and for suturing the valve 12 to the valve annulus in the heart. The ring 60 may be made from a biological material such as, for example, bovine or porcine pericardial tissue, or from a suitable synthetic material, such as the material marketed under the tradename DACRON or the material marketed under the tradename TEFLON. In the embodiment of FIG. 3, the ring 60 is positioned underneath the proximal edge 62 of the conduit 20. Alternatively, the ring 60 could be positioned on top of the proximal edge 62, as shown in FIG. 3A, or wrapped around the proximal edge, as shown in FIG. 3B, and subsequently sutured in place.

Figure 3C:
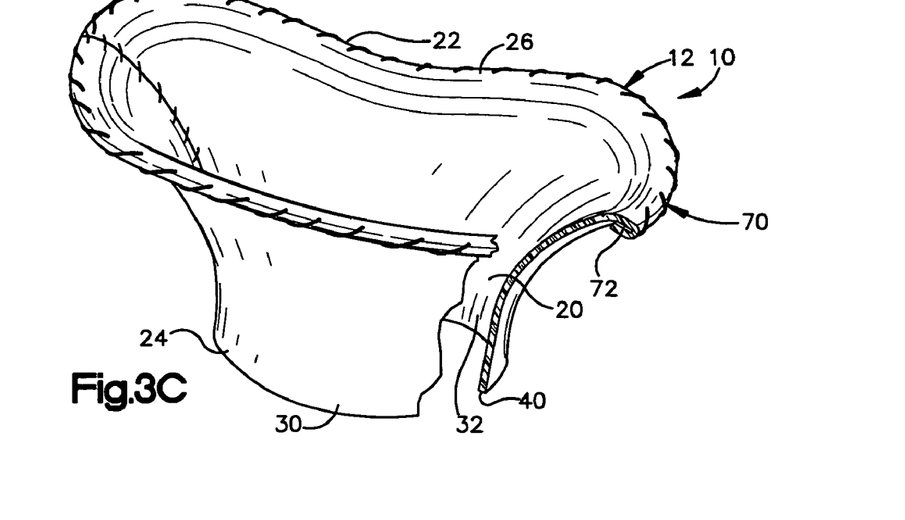
FIG. 3C is a perspective view, partially in section, of the valve of FIG. 1 and illustrating another method for forming a ring at the proximal end of the valve

According to an alternate construction for the valve 12 shown in FIG. 3C, a ring 70 is formed at the proximal end 22 of the conduit 20 by folding an additional portion 72 of the conduit 20 located at the proximal end 22 over onto itself and suturing the folded portion to the conduit.

Replacement of the native mitral valve 14 (FIG. 4) with the bioprosthetic valve 12 begins by taking either direct or echocardiographic measurements of the height of the anterior and posterior leaflets 34 and 36 of the native mitral valve. The size of the bioprosthetic valve 12 to be implanted is determined based on a measurement of the distance between the right and left trigones on the valve annulus. Four stay-sutures (6-0 silk) may be placed on the annulus of both mitral commissures and on the centers of the anterior and posterior leaflets 34 and 36 to help make sure that the bioprosthetic valve 12 is implanted in the proper anatomical orientation.

Figure 4:
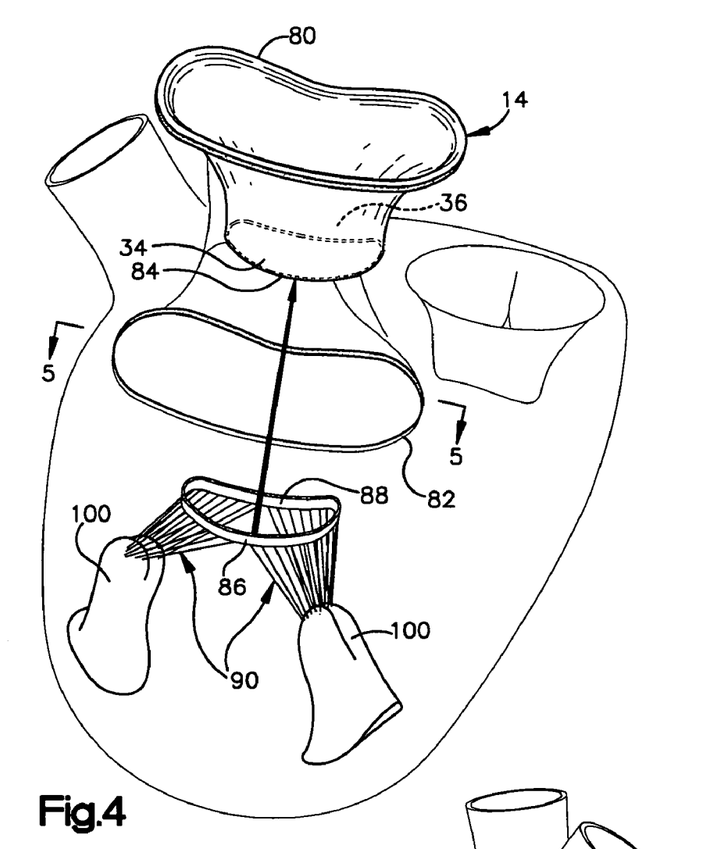
FIG. 4 is a perspective view of the left ventricle illustrating the native mitral valve being resected in accordance with the present invention.
Figure 5:
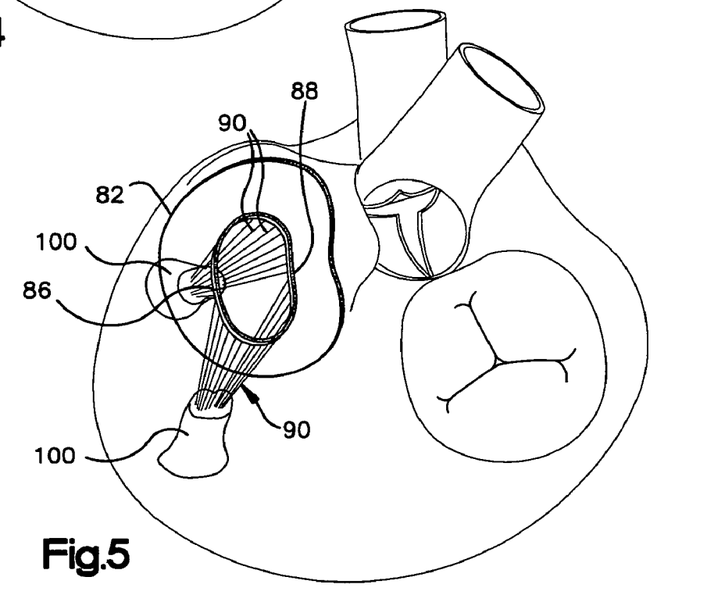
FIG. 5 is a plan view of FIG. 4 following resection of the native mitral valve.

As may be seen in FIGS. 4 and 5, the native mitral valve 14 is then dissected from the heart. The proximal end 80 of the native mitral valve 14 is resected from the valve annulus 82. At the distal end 84 of the native mitral valve 14, the anterior and posterior leaflets 34 and 36 are resected in such a manner that the free edges 86 and 88 of the anterior and posterior leaflets, respectively, remain intact and connected to the native chordae tendineae 90 which, in turn, remain attached to the two papillary muscles 100.

Figure 6:
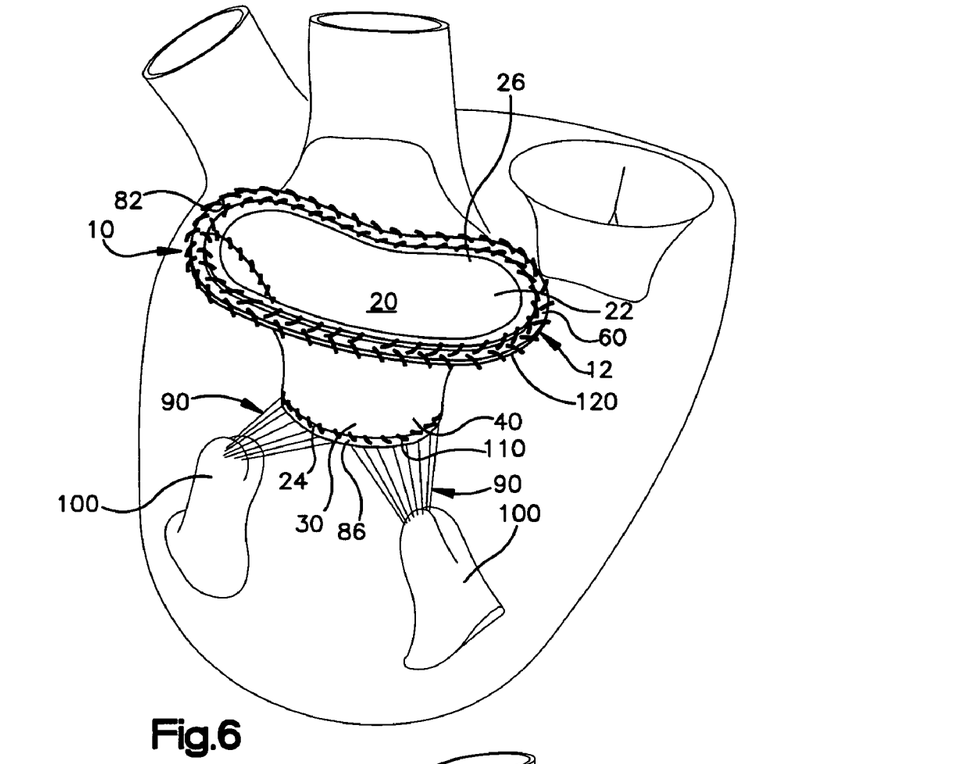
FIG. 6 is a perspective view of the valve of FIG. 1 implanted in the native mitral annulus shown in FIG. 4.

Next, the prosthetic valve 12 is moved into the position shown in FIG. 6. The second annulus 40 of the conduit 20 (at the distal end 24 where the first and second leaflets 30 and 32 terminate) is then sutured to the free edges 86 and 88 of the anterior and posterior leaflets 34 and 36 of the native mitral valve 14 that were preserved during the resection of the native mitral valve. According to one technique, 5-0 Ethibond continuous over-and-over sutures 110 may be used to secure the distal end 24 of the prosthetic valve 12 to the free edges 86 and 88. The sutures 110 may be started from the apex of the first and second leaflets 30 and 32 and extended toward both commissural sides to help prevent any folds from occurring in the first and second leaflets.

Figure 7:
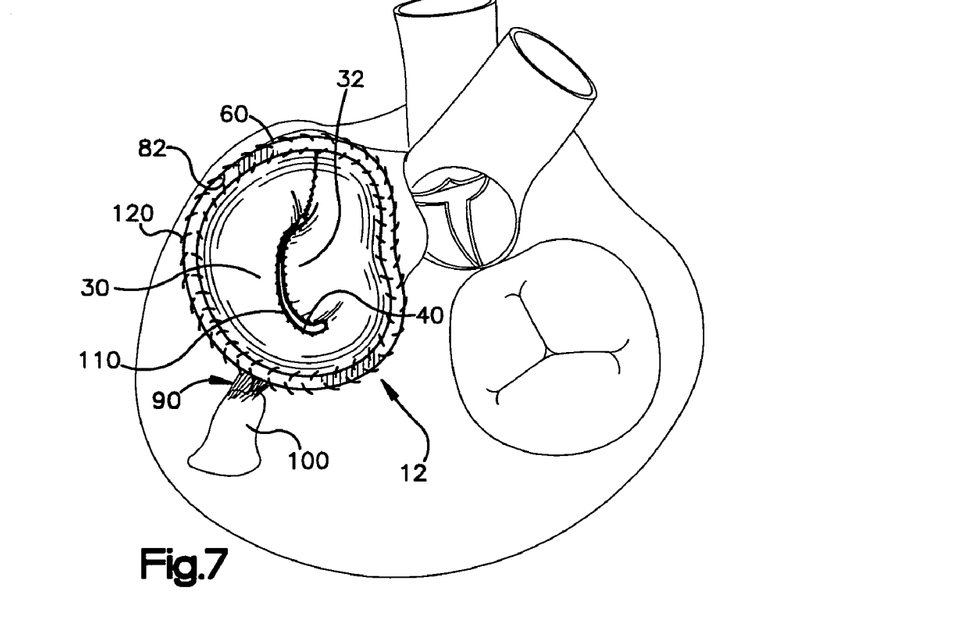
FIG. 7 is a plan view of the valve of FIG. 1 implanted in the native mitral annulus shown in FIG. 4.

To complete the replacement procedure, the ring 60 at the proximal end 22 of the bioprosthetic valve 12 is sewn to the native mitral annulus 82 as shown in FIGS. 6 and 7 with sutures 120. The sutures 120 may be three 4-0 Prolene running sutures or other suitable means. Once it is sutured to the valve annulus 82, the ring 60 functions to impede dilatation of the valve annulus and preserve the motion of the valve annulus.

The prosthetic valve 12 and associated method for replacing the native mitral valve 14 described above are useful in treating dilated cardiomyopathy, ischemic cardiomyopathy, ischemic mitral valve regurgitation, and infected mitral valve endocarditis. By suturing the second annulus 40 at the distal end 24 of the valve 12 to the free edges 86 and 88 of the anterior and posterior leaflets 34 and 36 of the native mitral valve 14 that are intentionally left intact when the native mitral valve is resected, the native chordae tendineae 90, which remain attached to the papillary muscles 100, continue to provide prolapse prevention and left ventricular muscle support functions. Significantly, the bioprosthetic valve 12 and the method for implanting the bioprosthetic valve described herein accomplish the goal of maintaining the continuity between the valve annulus 82 and the papillary muscles 100.

Additional benefits of the bioprosthetic valve 12 and associated method for implanting include:

A) a large orifice with an adequate circumference correlated with the size of the patient's body surface area, unrestrictive to a central free flow, compatible with high cardiac output at exercise, a low pressure required to open the valve, and without an increased gradient across the valve;

B) rapid opening and closure at all pressure ranges, without regurgitate flow and obstruction of the left ventricle outflow tract;

C) no rigid support or stent in the mitral area to allow the physiologic contraction of the left ventricular posterior wall around the mitral annulus during systole, flexible to adapt precisely to the mitral annulus reducing the tissue stress and allowing a uniform distribution of stress on the prosthetic valve which provides longer life and a higher resistance to wear, tear, and calcification; and F) anticoagulation treatment is not required and no trauma of the blood elements is produced.

Figure 8:
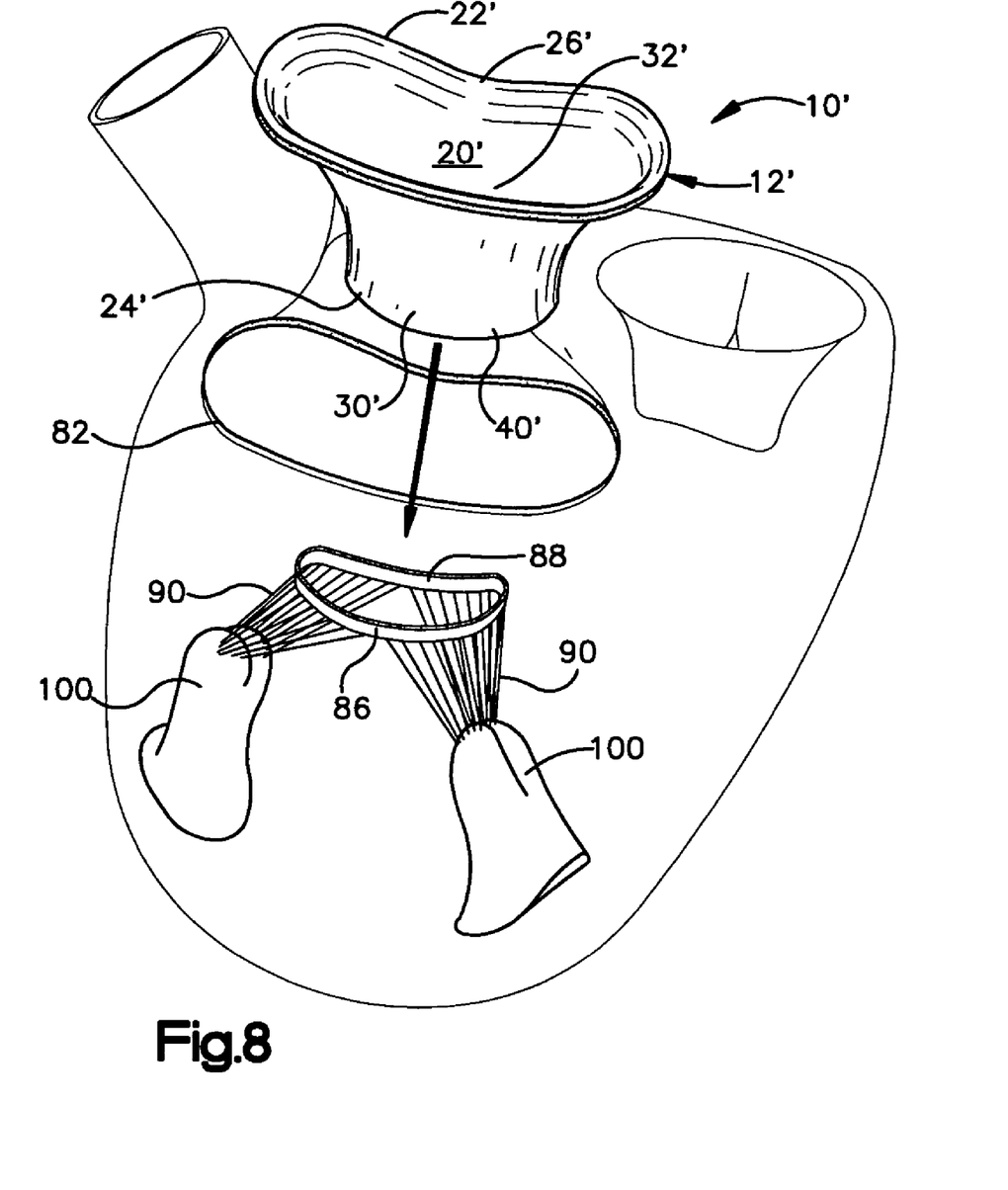
FIG. 8 is a perspective view of a stentless, bioprosthetic valve in accordance with a second embodiment of the present invention.
Figure 9:
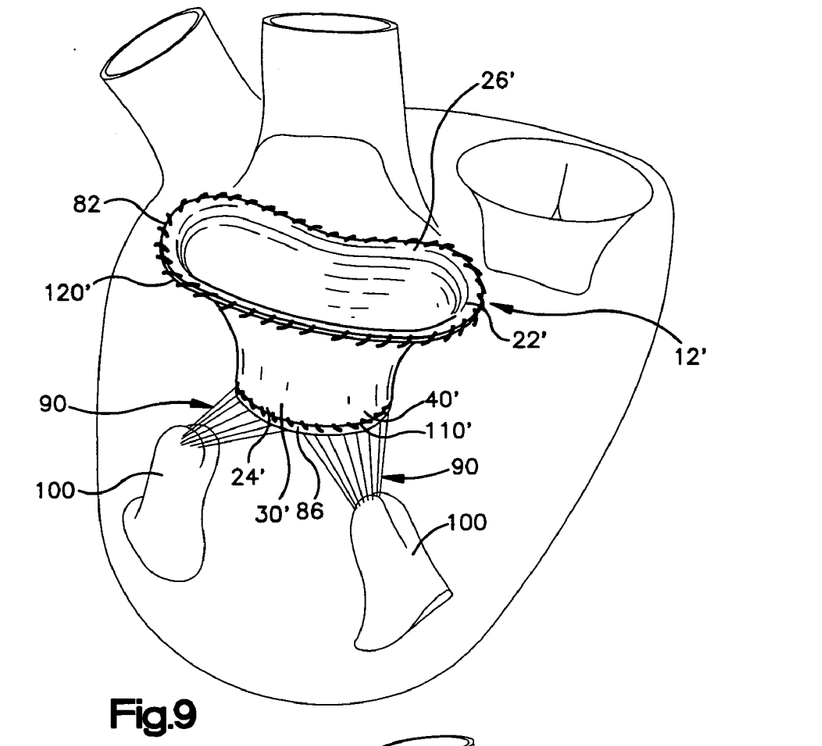
FIG. 9 is a perspective view of the valve of FIG. 8 implanted in the native mitral annulus shown in FIG. 4.
Figure 10:
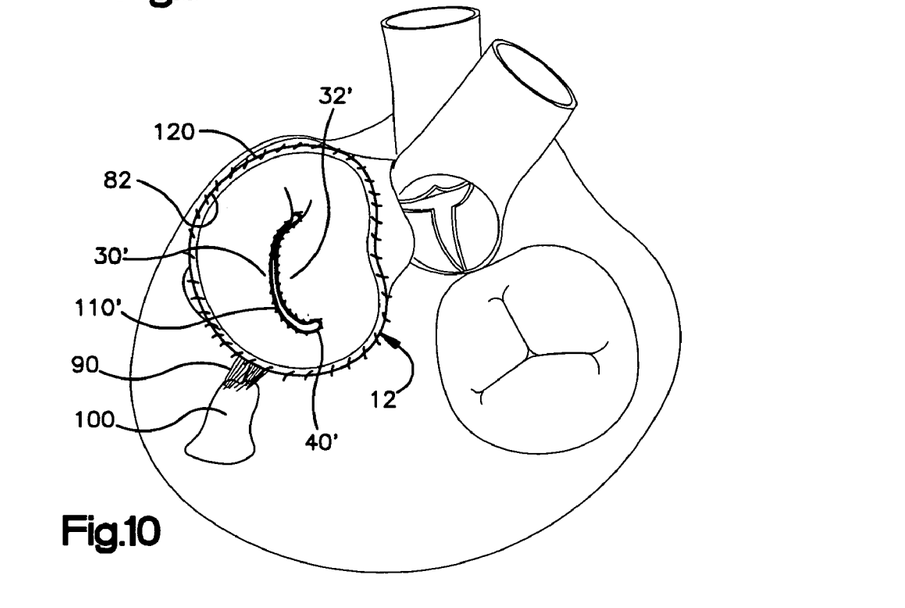
FIG. 10 is a plan view of the valve of FIG. 8 showing the valve implanted in the native mitral annulus shown in FIG. 4.

FIGS. 8–10 illustrate an apparatus 10' comprising a stentless bioprosthetic valve 12' in accordance with a second embodiment of the present invention in which the bioprosthetic valve comprises a homograft mitral valve. In FIGS. 8–10, reference numbers that are the same as those used in FIGS. 1–7 indicate structure that is the same as described above for the previous embodiment, while reference numbers that have apostrophe (') indicate similar, but not identical, structure.

In accordance with the second embodiment, the homograft valve 12' to be implanted must be harvested. To harvest the valve 12', the left atrium of the donor heart is opened and the mitral valve annulus 82, the leaflets 30' and 32', and the subvalvular tissues (the chordae tendineae 90 and the papillary muscles 100) are anatomically evaluated. The valve 12', and in particular the heights of the leaflets 30' and 32', are measured.

The left ventricle is then opened and the entire valve 12' is excised or removed by incision of the valve circumferentially (not shown). The incision is placed near the fibrous valve annulus 82 of the valve 12' and then through the myocardium of the left atrium and ventricle to ensure that the valve annulus is preserved intact. The donor chordae tendineae that remain attached to the valve leaflets 30' and 32' are removed from the tips of the papillary muscles and the valve 12' is placed on ice. After the mitral valve 12' is thawed, the donor chordae tendineae are trimmed to form the distal edges of the homograft leaflets 30' and 32' that will be attached to the free edges 86 and 88 of the native mitral valve 14. The myocardium of the atrium and ventricle is then cut away from the first annulus 26' of the valve 12', leaving just enough tissue to allow sewing of the homograft valve, without damaging the leaflets 30' and 32', to the native mitral valve annulus 82.

In an identical fashion to the first embodiment, the native mitral valve 14 is dissected from the heart as shown in FIG. 4. The proximal end 80 of the native mitral valve 14 is resected from the valve annulus 82. At the distal end 84 of the native mitral valve 14, the anterior and posterior leaflets 34 and 36 are resected in such a manner that the free edges 86 and 88 of the anterior and posterior leaflets, respectively, remain intact and connected to the native chordae tendineae 90 which, in turn, remain attached to the two papillary muscles 100.

Next, the valve 12' is moved into the position shown in FIG. 9. The second annulus 40' (at the distal end 24' where the first and second leaflets 30' and 32' terminate) is then sutured to the free edges 86 and 88 of the anterior and posterior leaflets 34 and 36 of the native mitral valve 14 that were preserved during the resection of the native mitral valve. According to one technique, 5-0 Ethibond continuous over-and-over sutures 110' may be used to secure the distal end 24' of the homograft valve 12' to the free edges 86 and 88. The sutures 110' may be started from the apex of the first and second leaflets 30' and 32' and extended toward both commissural sides to help prevent any folds from occurring in the first and second leaflets.

The proximal end 22' of the valve' 12 is then sewn to the native mitral annulus 82 as shown in FIGS. 9 and 10 with sutures 120'. The sutures 120 may be 4-0 Prolene or polypropylene running or continuous sutures or other suitable means. A ring, such as the ring 60 described above or another suitable annuloplasty ring may be sutured in at the valve annulus 82 to impede dilatation of the valve annulus and preserve the motion of the valve annulus.

The homograft valve 12' and the associated method for replacing the native mitral valve 14 described above are useful in treating dilated cardiomyopathy, ischemic cardiomyopathy, ischemic mitral valve regurgitation, and infected mitral valve endocarditis. By suturing the second annulus 40' at the distal end 24' of the valve 12' to the free edges 86 and 88 of the anterior and posterior leaflets 34 and 36 of the native mitral valve 14 that are intentionally left intact when the native mitral valve is resected, the native chordae tendineae 90, which remain attached to the papillary muscles 100, continue to provide prolapse prevention and left ventricular muscle support functions. Significantly, the homograft valve 12' and the method for implanting the homograft valve described herein also maintain the continuity between the valve annulus 82 and the papillary muscles 100.

From the above description of the invention, those skilled in the art will perceive improvements, changes and modifications. Such improvements, changes and modifications within the skill of the art are intended to be covered by the appended claims.

Having described the invention, we claim:

1. A stentless bioprosthetic valve for replacing a native mitral valve resected from a valve annulus in a heart, the native mitral valve having anterior and posterior leaflets that extend from the valve annulus at a proximal end to free edges at a distal end, the native mitral valve being resected so that the free edges and associated native chordae tendineae remain intact, the free edges forming a ring from which the native chordae tendineae extend to native papillary muscles, said bioprosthetic valve comprising:

at least one piece of biocompatible material comprising an unstented a bi-leaflet conduit having dimensions that correspond to the dimensions of the native leaflets of the native mitral valve, said conduit having a proximal end and a distal end, said proximal end and said distal end being spaced apart by a distance corresponding to the dimensions of the native mitral valve leaflets, said proximal end of said conduit defining a first annulus;

a biocompatible, unstented ring connected to said first annulus for supporting said first annulus and for suturing to the valve annulus in the heart, said ring, when sutured to the valve annulus, impeding dilatation of the valve annulus and preserving motion of the valve annulus;

said conduit further including first and second leaflets that mimic the three-dimensional anatomical shape of the anterior and posterior leaflets of the native mitral valve, said first and second leaflets extending between said proximal end and said distal end of said conduit;

said distal end of said conduit defining a second annulus at which said first and second leaflets terminate and which does not include bioprosthetic chordae tendineae, said second annulus configured to be sutured to the ring formed by the free edges of the anterior and posterior leaflets at the distal end of the native mitral valve that remain intact following resection of the native mitral valve so that the native chordae tendineae, which are attached to the papillary muscles, continue to provide prolapse prevention and left ventricular muscle support functions in addition to maintaining the continuity between the valve annulus and the papillary muscles, whereby the entire circumference of said second annulus formed at said distal end by said first and second leaflets is spaced from the papillary muscles; and wherein said ring is formed from at least one piece of said bi-leaflet conduit that has been folded over itself and sutured at the proximal end of said conduit.

2. A method for replacing a native mitral valve with a stentless bioprosthetic valve, the native mitral valve having anterior and posterior leaflets that extend from a valve annulus at a proximal end to free edges at a distal end, said method comprising the steps of:

providing at least one piece of biocompatible material that comprises a bi-leaflet conduit having dimensions that correspond to the dimensions of the native mitral valve being replaced, the conduit having a proximal end and a distal end, the proximal end defining a first annulus and the distal end defining a second annulus, the conduit further including first and second leaflets that mimic the three-dimensional shape of the anterior and posterior leaflets of the native mitral valve, the first and second leaflets extending from the proximal end and terminating at the distal end of the conduit;

resecting the majority of the native anterior and posterior leaflets of the native mitral valve with a circumferential resection at the proximal end of the native leaflets that releases the proximal end of the native leaflets from the valve annulus and another circumferential resection of the distal end of the native leaflets that leaves the free edges of the native anterior and posterior leaflets intact along with the native chordae tendineae, which are attached to the papillary muscles, so that the native chordae tendineae can provide prolapse prevention and left ventricular muscle support functions for the bioprosthetic valve in addition to maintaining the continuity between the valve annulus and the papillary muscles;

suturing the first and second leaflets at the second annulus of the conduit to the free edges of the anterior and posterior leaflets of the native mitral valve that remain following resection of the native mitral valve; and suturing the first annulus of the conduit to the valve annulus of the native mitral valve to secure the bioprosthetic valve to the valve annulus.

3. The method of claim 2 further comprising the steps of:
providing a biocompatible, unstented support ring that encircles the first annulus; and suturing the support ring to the valve annulus of the heart to secure the bioprosthetic valve to the valve annulus and to impede dilatation of the valve annulus and preserve motion of the native mitral valve annulus.

4. The method of claim 3 wherein said step of providing a support ring includes the steps of:

folding a portion of the biocompatible material at the proximal end of the conduit over onto itself; and suturing the folded portion to the conduit about the first annulus.

5. The method of claim 3 wherein said step of providing a support ring includes the steps of:

providing a separate ring-shaped piece of biocompatible material; and suturing the ring-shaped piece about said first annulus.

* * * * *

UNITED STATES PATENT AND TRADEMARK OFFICE
CERTIFICATE OF CORRECTION

| | |
|---|---|
| PATENT NO. | : 7,087,079 B2 |
| APPLICATION NO. | : 10/683105 |
| DATED | : August 8, 2006 |
| INVENTOR(S) | : Jose' Luis Navia et al. |

It is certified that error appears in the above-identified patent and that said Letters Patent is hereby corrected as shown below:

Column 8, line 40, after "comprising" delete "an".

Column 8, line 41, before "a bi-leaflet" delete "unstented".

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,087,079 B2
APPLICATION NO. : 10/683105
DATED : August 8, 2006
INVENTOR(S) : Jose' Luis Navia et al.

It is certified that error appears in the above-identified patent and that said Letters Patent is hereby corrected as shown below:

Column 8, line 40, after "comprising" insert --an unstented--.

Column 8, line 41, before "a bi-leaflet" delete "a".

Signed and Sealed this

Fifth Day of January, 2010

David J. Kappos
*Director of the United States Patent and Trademark Office*